United States Patent
Wang et al.

(10) Patent No.: US 9,000,004 B2
(45) Date of Patent: Apr. 7, 2015

(54) AMBROXOL HYDROCHLORIDE COMPOSITION AND ITS PREPARATION METHOD

(71) Applicant: Hainan Weikang Pharmaceutical (Qianshan) Co., Ltd., Anhui (CN)

(72) Inventors: Liuyi Wang, Anhui (CN); Jincan Wang, Anhui (CN)

(73) Assignee: Hainan Weikang Pharmaceutical (Qianshan) Co., Ltd., Anhui (CN)

( * ) Notice: Subject to any disclaimer, the term of this patent is extended or adjusted under 35 U.S.C. 154(b) by 0 days.

(21) Appl. No.: 14/237,500

(22) PCT Filed: Sep. 28, 2012

(86) PCT No.: PCT/CN2012/082337
§ 371 (c)(1),
(2) Date: Feb. 6, 2014

(87) PCT Pub. No.: WO2013/177880
PCT Pub. Date: Dec. 5, 2013

(65) Prior Publication Data
US 2014/0206710 A1    Jul. 24, 2014

(30) Foreign Application Priority Data
May 28, 2012 (CN) .......................... 2012 1 0169279

(51) Int. Cl.
*A61K 31/137* (2006.01)
*A61K 31/138* (2006.01)
*A61K 31/439* (2006.01)
*A61K 31/46* (2006.01)

(52) U.S. Cl.
CPC ............. *A61K 31/138* (2013.01); *A61K 31/137* (2013.01); *A61K 31/46* (2013.01); *A61K 31/439* (2013.01)

(58) Field of Classification Search
None
See application file for complete search history.

(56) References Cited

FOREIGN PATENT DOCUMENTS

EP   1417961  *  5/2004  ........... A61K 31/165

OTHER PUBLICATIONS

Merck Index 1895, p. 36.*
Balsamo et al. (Eur Respir Rev 2010; 19(116):127-133).*

* cited by examiner

*Primary Examiner* — Ernst V Arnold
(74) *Attorney, Agent, or Firm* — Wang Law Firm, Inc.; Li K. Wang; Stephen Hsu

(57) ABSTRACT

An ambroxol hydrochloride composition and a preparation method therefor. 0.1%-99.9% by mass of ambroxol hydrochloride and 99.9%-0.1% by mass of scopolamine serving as main ingredients and mannitol are added into water for injection; dissolve, then adjust to pH 5.0; add 0.1% of activated carbon with stirring; filter out the activated carbon, and then filter the liquid; send into a lyophilizer, cool to −40° C., and hold the temperature for 2 hours; warm to −5° C. to 0° C. slowly to lyophilize the liquid, heat to 35° C., and hold the temperature for 3 hours; take out of the lyophilizer to obtain a lyophilized powder injection containing ambroxol hydrochloride and scopolamine; crush the lyophilized powder injection under sterile conditions, and sieve to obtain sterile lyophilized powder containing ambroxol hydrochloride and scopolamine; and prepare various dosage forms by using the lyophilized powder as a raw material.

2 Claims, No Drawings

AMBROXOL HYDROCHLORIDE COMPOSITION AND ITS PREPARATION METHOD

BACKGROUND OF THE INVENTION

1. Field of Invention

The present invention relates to the field of medicine, and more particularly to a compound ambroxol hydrochloride composition and a preparation method therefor.

2. Related Art

Chronic obstructive pulmonary disease (COPD) is a preventable and treatable disease characteristic with airflow limitation, and the airflow limitation is not fully reversible and shows progressive development. COPD mainly involves lungs, but can also cause systemic (or referred to as extrapulmonary) adverse effects. COPD is a common respiratory tract disease. The old are susceptible to COPD because they have an airway mucociliary clearance dysfunction and a lung oxidation dysfunction as they become aged.

Tobacco smoke and other chronic irritants have effects on lungs to cause abnormal inflammatory responses in the lungs. COPD may involve airways, lung parenchyma and pulmonary vessels, manifesting development of chronic inflammation characteristic with neutrophils, macrophages, and lymphocytes infiltration. The inflammatory mediators released by these cells interact with structure cells in airways and lung parenchyma, thereby promoting the accumulation of T lymphocytes (especially CD+8) and neutrophils and eosinophils in the lung tissue, and the release of leukotriene B4 (LTB4), interleukin8 (IL-8), tumor necrosis factor-$\alpha$ (TNF-$\alpha$) and other mediators, causing lung structural damage. COPD lung inflammation may be aggravated further and airflow may be limited due to oxidation-oxidation imbalance, protease-antiprotease imbalance, autonomic nervous system dysfunction, and increased cholinergic tone. Genetic susceptibility plays a role in the pathogenesis of COPD.

COPD is implicated with central airways, peripheral airways, lung parenchyma, and pulmonary vessels. Epithelial inflammatory cell infiltration occurs on central airways (trachea, bronchi, and bronchioles with diameter greater than 2-4 mm) surfaces, and the mucus secretion increases as the mucus gland enlarges and goblet cells increase. The chronic inflammation in the peripheral airways (bronchi and bronchioles with diameter less than 2 mm) causes airway wall damage and repeated repair processes. Airway wall structural remodeling occurs during the repair processes, collagen content increases and scar tissue is formed, all of these changes cause the airways to narrow, resulting in fixed airway obstruction.

COPD lung parenchyma involvement manifests centrilobular emphysema, which involves respiratory bronchioles, and causes lumen expansion and destruction. When the disease is mild, lesions often occur in the upper area of the lungs, and when disease progresses, it may involve the entire lungs, accompanied by the destruction of the pulmonary capillary bed.

Changes in the COPD pulmonary vessels which are characteristic with thickness increase of the blood vessel wall can occur early, which manifest intimal thickening, smooth muscle proliferation and vascular wall inflammatory cell infiltration. When secondary pulmonary heart disease is developed in the late stages, there may be multiple in situ thrombosis in pulmonary arterioles. Acute exacerbation of COPD is often complicated with deep vein thrombosis and pulmonary thromboembolism.

SUMMARY OF THE INVENTION

An objective of the present invention is to provide a compound ambroxol hydrochloride composition and a preparation method therefor. The compound preparation is used to treat chronic obstructive pulmonary disease, and has a strong synergy effect and rapid effect.

Technical solutions of the present invention are:

A compound ambroxol hydrochloride composition, characterized in that main ingredients of the composition are 0.1%-99.9% by mass of ambroxol hydrochloride and 99.9%-0.1% by mass of scopolamine.

A method for preparing a compound preparation by using a compound ambroxol hydrochloride composition, characterized in that specific steps are:

a. adding 0.1%-99.9% of ambroxol hydrochloride, 99.9%-0.1% of scopolamine and 5 to 10 times the main ingredients of mannitol to water for injection;

b. stirring to dissolve, adjusting to pH 5.0 by adding an NaOH solution;

c. adding 0.1% of activated carbon with stirring for 30 minutes;

d. filtering out the activated carbon, and then filtering the liquid with 0.45 µm and 0.22 µm microporous filter membranes;

e. filling the filtered liquid to a large plate or vial;

f. sending into a lyophilizer, cooling to −40° C., and holding the temperature for 2 hours;

g. warming to −5° C. to 0° C. slowly to lyophilize the liquid, heating to 35° C., and holding the temperature for 3 hours;

h. taking out of the lyophilizer after lyophilizing to obtain a lyophilized powder injection containing ambroxol hydrochloride and scopolamine;

i. crushing the lyophilized powder injection under a sterile condition, sieving with a 180- mesh sieve to obtain sterile lyophilized powder containing ambroxol hydrochloride and scopolamine; and j. preparing various dosage forms by using the lyophilized powder as a raw material.

The dosage forms include tablets, tinctures, suppositories, capsules, ointments, creams, pastes, ophthalmic preparations, pills, implantations, syrups, aerosols, powder inhalations, sprays, films, granules, oral solutions, oral suspensions, oral emulsions, powders, and nasal preparations.

Ambroxol hydrochloride mainly acts on respiratory secretory cells, regulates secretion of mucinous and serous substances, thereby increasing serous secretion. It can also cleave polysaccharide fibers of acid glycoprotein in sputum, inhibit acidic protein synthesis in mucus glands and goblet cells, and decrease viscosity of sputum, so that mucus becomes thin and easy to discharge. It can also increase movement frequency and intensity of respiratory cilia, facilitate mucus discharge, and increase respiratory self-purification. Further, ambroxol hydrochloride has significant antioxidant activities, and plays an important role in the pathogenesis of lung diseases caused by reactive free oxygen radicals. It can clear oxide H-, and Hocl reduces hyperreactivity to mucosal bronchial damage, thereby stimulating PS secretion in cells. In addition, ambroxol also activates intracellular glutathione system, and facilitates intracellular glutathione (GSH) synthesis, thereby resisting the damage caused by oxygen free radicals.

Scopolamine may have antagonism against oxygen free radicals produced by damaged cells, and have antioxidant activities and superoxide scavenging effects. In long-term studies on adult rat cardiac muscle exposure to pyrogallol, it is found that scopolamine can effectively inhibit superoxide generation and myocardial dysfunction caused by pyrogallol, and has a certain effect on heart dysfunction caused by oxygen free radicals. Scopolamine can reduce LPO content in the kidney venous blood of a rabbit experiencing ischemia-reperfusion, reduce the lipid peroxidation caused by free radicals, and provide protection against rabbit renal ischemia-reperfusion injury; it can prevent thiol on erythrocyte membrane protein in rats from damages by exogenous H2O2; it have a significant dose-dependent scavenging effect on superoxide anion radicals produced by a hypoxanthine-xanthine oxidase system, and the clearing effect is slightly lower than that on superoxide dismutase (SOD).

Scopolamine not only inhibits lipopolysaccharide (LPS)-induced endothelial cell expression of plasminogen activator inhibitor 1 (Pal-1) protein and mRNA expression, but also inhibits the basal level of Pal-1 expression, and thus plays a role in anti-thrombosis. Scopolamine may inhibit the increase of LPS-induced endothelial cell expression of Pal-1 through NF-κB pathway. Scopolamine can inhibit the synthesis of thromboxane B2, prevent platelet aggregation and release, prevent micro-thrombosis, and inhibit deposition of antigen-antibody complex.

Scopolamine has the effect of relaxing smooth muscle, relieving blood vessel spasm, and improving microcirculation, and can inhibit glandular secretion. Scopolamine can act on cholinergic receptors on the airway mucosa and the smooth muscle, effectively inhibit cholinergic nerve function of the airway, reduce vagal tone, and facilitate dilation of bronchi, capillary bronchi and the decrease of airway secretions, so as to relieve breath, reduce bell sound asthma, improve clinical symptoms, and promote recovery from the disease. In addition, scopolamine has many good effects, including sedation of the cerebral cortex, reduction of oxygen consumption, relief from small artery spasm, improvement in brain tissue hypoxia, blockage of multiorgan dysfunction and so on.

The preparation method provided by the present invention is scientific and reasonable, and is convenient for preparing various dosage forms. The compound preparation prepared with the method can: 1) reduce the viscosity of sputum so as to make sputum thin and promote mucus discharge, thereby improving respiratory self-purification; 2) increase the anti-oxidation effect of the human body, and help COPD patients to enhance their immune systems; 3) excite respiratory center, relieve bronchial and vascular smooth muscle spasm, decrease preload and post load of heart, promote recovery of the cardiac function, relieve small artery spasm of heart, brain, lungs, kidneys and other tissues, improve microcirculation and tissue hypoxia status, and improve clearance of airway epithelial surface, thereby preventing and treating COPD.

DETAILED DESCRIPTION OF THE INVENTION

The present invention will be illustrated further with reference to specific embodiments, in order to make technical means, creative features, purposes and effects achieved by the present invention easy to understand.

Embodiment 1: Preparation of a Lyophilized Powder Injection Containing Ambroxol Hydrochloride and Scopolamine, Based on 1000 Injections 1. Prescription

| Name | Dosage |
|---|---|
| Ambroxol hydrochloride | 15 g |
| Scopolamine | 0.02 g |
| Mannitol | 100 g |
| Water for injection | 2000 ml |

2. Preparation process

The prescribed amounts of ambroxol hydrochloride, scopolamine and mannitol were added to water for injection, dissolved with stirring, and then adjusted to pH 5.0 by adding an NaOH solution. 0.1% of activated carbon was added with stirring for 30 minutes, and then was filtered out. The liquid was filtered with 0.45 μm and 0.22 μm mircroporous filter membranes, filled into a container, sent into a lyophilizer, and cooled to −40° C.; the temperature was held for 2 hours, and the liquid was warmed to −5° C.-0° C. slowly to lyophilize, and heated to 35° C.; the temperature was held for 3 hours, and the product was taken out of the container after lyophilizing.

Embodiment 2: Preparation of a Tablet Containing Ambroxol Hydrochloride and Scopolamine, Based on 1000 Tablets 1. Prescription

| Name | Dosage |
|---|---|
| Ambroxol hydrochloride | 15 g |
| Scopolamine | 0.02 g |
| Microcrystalline cellulose | 30 g |
| Crosslinked povidone | 10 g |
| Hydroxypropyl cellulose | 10 g |
| Mannitol | 30 g |
| Sucralose | 1 g |
| Menthol | 1 g |
| Lactose | 50 g |
| Magnesium stearate | 5 g |
| Silica | 1 g |

2. Preparation process

The prescribed amounts of ambroxol hydrochloride, scopolamine and mannitol were added to water for injection, stirred to dissolve, and then adjusted to pH 5.0 by adding an NaOH solution. 0.1% of activated carbon was added with stirring for 30 minutes, and then filtered out. The liquid was filtered with 0.45 μm and 0.22 μm mircroporous filter membranes, filled to a large plate, sent into a lyophilizer, and cooled to −40° C.; the temperature was held for 2 hours, and the liquid was warmed to −5° C.-0° C. slowly to lyophilize, and heated to 35° C.; the temperature was held for 3 hours, and the product was taken out of the lyophilizer after lyophilizing. The lyophilized preparation in the large plate was crushed under a sterile condition, and sieved with a 180-mesh sieve to obtain sterile lyophilized powder containing ambroxol hydrochloride and scopolamine.

The prescribed amounts of sucralose and menthol were mixed, the lyophilized powder containing ambroxol hydrochloride and scopolamine was added and mixed well, and then microcrystalline cellulose, lactose crosslinked povidone, hydroxypropyl cellulose were added and mixed well, finally magnesium stearate, silica were added and mixed well. The tablets were prepared by using a direct compression method, during which the humidity is controlled below 50%.

Embodiment 3: Preparation of an Injection Containing Ambroxol Hydrochloride and Scopolamine, Based on 1000 Injections 1. Prescription

| Name | Dosage |
|---|---|
| Ambroxol hydrochloride | 15 g |
| Scopolamine | 0.02 g |
| Sodium chloride | 16 g |
| Water for injection | 2000 ml |

2. Preparation process

The prescribed amounts of ambroxol hydrochloride, scopolamine and mannitol were added to water for injection, stirred to dissolve, and then adjusted to pH 5.0 by adding an NaOH solution. 0.1% of activated carbon was added with stirring for 30 minutes, and then filtered out. The liquid was filtered with 0.45 μm and 0.22 μm mircroporous filter membranes, filled to a large plate, sent into a lyophilizer, and cooled to −40° C.; the temperature was held for 2 hours, and the liquid was warmed to −5° C.-0° C. slowly to lyophilize, and heated to 35° C.; the temperature was held for 3 hours, and the product was taken out of the lyophilizer after lyophilizing. The lyophilized preparation in the large plate was crushed under a sterile condition, sieved with a 180-mesh sieve to obtain sterile lyophilized powder containing ambroxol hydrochloride and scopolamine.

The lyophilized powder and sodium chloride were added to water for injection to 80%, and stirred to dissolve. 0.05% activated carbon was added and stirred to adsorb for 15 minutes, and filtered out coarsely. The liquid was adjusted to pH 4.5-5.5 by using citric acid-disodium hydrogen phosphate buffer solution (pH 4.0), and water for injection was added to the full amount. The liquid was filtered with a 0.22 μm fine filter membrane. The filtrate was determined to be qualified with respect to pH, osmotic pressure and content, filled in a 2 ml ampoule and sealed, and sterilized at 121° C. for 15 minutes.

The basic principles, main features and advantages of the present invention are shown and described above. Persons skilled in the art should understand that the present invention is not limited by the above embodiments. The embodiments described above and the specification only describes the principles of the present invention. Various modifications and improvements can be made to the present invention without departing from the spirit and scope of the present invention, and these modifications and improvements shall fall within the protection scope of the present invention. The protection scope of the present invention is defined by the appended claims and their equivalents.

What is claimed is:

1. A method, for preparing a composition, comprising the steps of:

a) adding 0.1%-99.9% of ambroxol hydrochloride, 99.9%-0.1% of scopolamine and 5 to 10 times main ingredients of mannitol to water to form a compound solution for injection;

b) stirring to dissolve the compound solution and adjusting pH of the compound solution to 5.0 by adding an NaOH solution;

c) adding 0.1% of activated carbon to the compound solution and stirring the compound solution for 30 minutes;

d) filtering out the activated carbon from the compound solution, and then filtering the compound solution with 0.45 μm and 0.22 μm microporous filter membranes;

e) filling the filtered compound solution into a large plate or vial;

f) sending the filtered compound solution into a lyophilizer, cooling to a first temperature of −40° C., and holding the first temperature for 2 hours;

g) warming the filtered compound solution slowly to −5° C. to 0° C. to lyophilize the filtered compound solution, heating the filtered compound solution to a second temperature of 35° C., and holding the second temperature for 3 hours;

h) taking the filtered compound solution out of the lyophilizer after lyophilizing to obtain a lyophilized powder injection containing ambroxol hydrochloride and scopolamine;

i) crushing the lyophilized powder injection under a sterile condition, sieving the lyophilized powder injection with a 180-mesh sieve to obtain a sterile lyophilized powder containing ambroxol hydrochloride and scopolamine; and j) preparing various dosage forms by using the sterile lyophilized powder as a raw material.

2. The method for preparing a composition according to claim 1, characterized in that the dosage forms comprise tablets, tinctures, suppositories, capsules, ointments, creams, pastes, ophthalmic preparations, pills, implantations, syrups, aerosols, powder inhalations, sprays, films, granules, oral solutions, oral suspensions, oral emulsions, powders, and nasal preparations.

* * * * *